United States Patent [19]

Schroeder et al.

[11] Patent Number: 5,355,215

[45] Date of Patent: Oct. 11, 1994

[54] METHOD AND APPARATUS FOR QUANTITATIVE FLUORESCENCE MEASUREMENTS

[75] Inventors: Kirk Schroeder; Brad Neagle, both of Ann Arbor, Mich.

[73] Assignee: Environmental Research Institute of Michigan, Ann Arbor, Mich.

[21] Appl. No.: 953,898

[22] Filed: Sep. 30, 1992

[51] Int. Cl.$^5$ .................... G01J 3/30; G01N 21/64
[52] U.S. Cl. .................... 356/317; 250/461.2; 356/417
[58] Field of Search .............. 356/317–318, 356/417, 244, 440, 344; 250/458.1, 459.1, 461.1, 461.2; 435/808, 291, 882

[56] References Cited

U.S. PATENT DOCUMENTS

| | | | |
|---|---|---|---|
| 3,604,927 | 9/1971 | Hirschfeld | 356/244 |
| 4,343,782 | 8/1982 | Shapiro | 424/3 |
| 4,573,796 | 3/1986 | Martin et al. | 356/318 |
| 4,626,684 | 12/1986 | Landa | 250/328 |
| 4,626,693 | 12/1986 | Hirschfeld | 250/458.1 |
| 4,713,781 | 12/1987 | Brizgis et al. | 364/552 |
| 4,758,727 | 7/1988 | Tomei et al. | 250/458.1 |
| 4,786,813 | 11/1988 | Svanberg et al. | 250/561.1 |
| 4,835,103 | 5/1989 | Cercek et al. | 435/29 |
| 4,877,965 | 10/1989 | Dandliker et al. | 250/458.1 |
| 5,051,162 | 9/1991 | Kambara et al. | 250/458.1 |
| 5,082,628 | 1/1992 | Andreotti et al. | 356/434 X |
| 5,091,652 | 2/1992 | Mathies et al. | 250/458.1 |
| 5,097,135 | 3/1992 | Makino et al. | 250/461.1 |
| 5,115,137 | 5/1992 | Andersson-Engels | 250/461.2 |
| 5,190,632 | 3/1993 | Fujimiya et al. | 356/344 |

FOREIGN PATENT DOCUMENTS

446972A2 9/1991 European Pat. Off. ............ 356/440
WO9015317 12/1990 PCT Int'l Appl. .

OTHER PUBLICATIONS

NTIS Alert, Jan. 28, 1992; 04,003–290.

*Primary Examiner*—Vincent P. McGraw
*Assistant Examiner*—K. P. Hantis
*Attorney, Agent, or Firm*—Krass & Young

[57] ABSTRACT

Measurement of the fluorescence of a layer of cells, disposed in a well, with supernatant liquid thereabove, is greatly enhanced in sensitivity by illuminating the cell layer with a beam of light incident thereupon at a first angle and detecting fluorescence emitted by the cells with a detector which views the illuminated cells at a second angle, wherein at least one of the first or second angles is oblique to the cell layer. By so controlling the geometry of the system, the contribution to background fluorescence by the supernatant liquid is greatly minimized. Sensitivity of the technique is further enhanced by restricting the portion of the illuminated cell layer which is viewed by the detector. The technique may be applied to an apparatus for rapidly scanning the fluorescence of a plurality of samples in a multiple well plate.

21 Claims, 4 Drawing Sheets

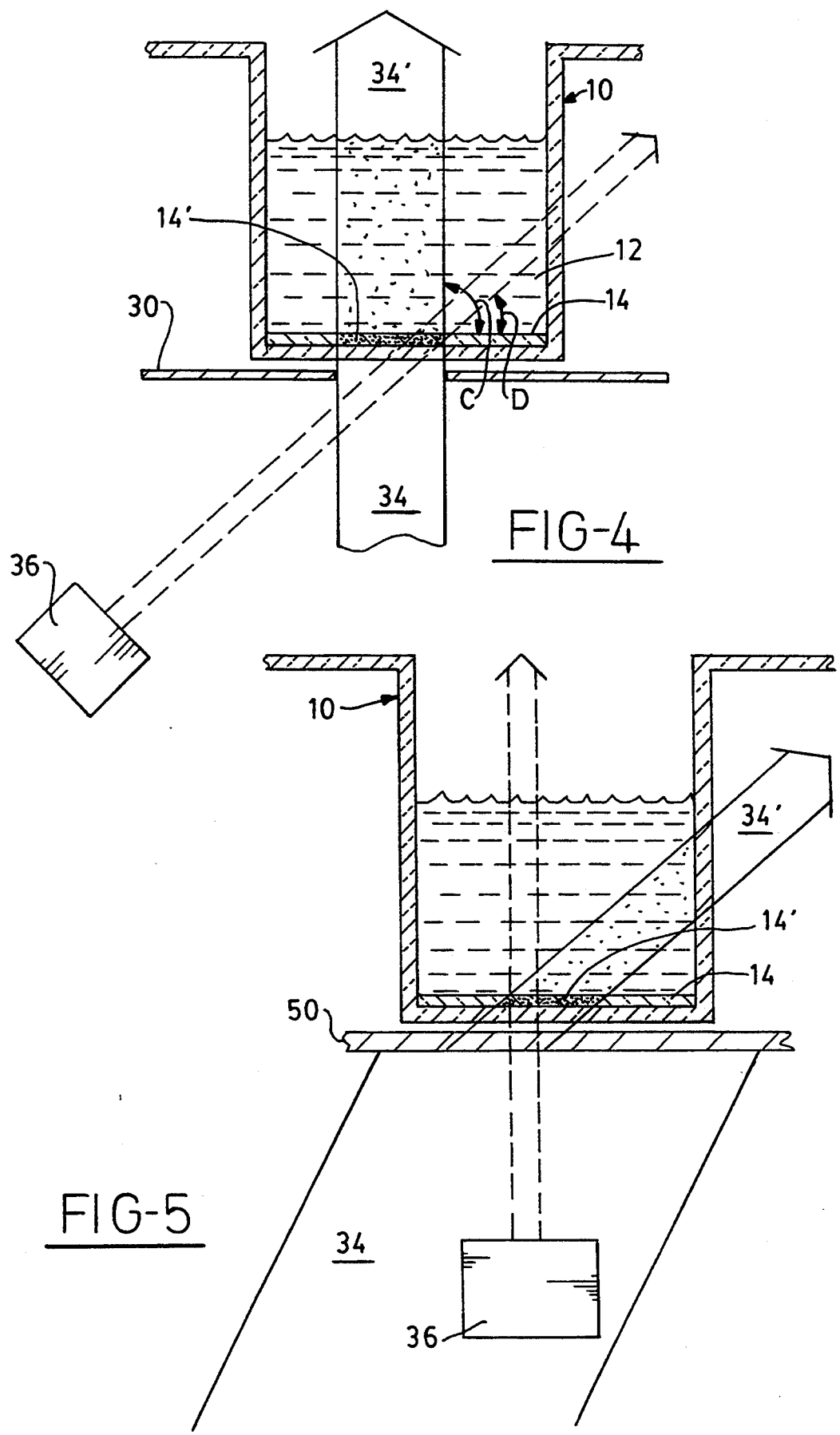

METHOD AND APPARATUS FOR QUANTITATIVE FLUORESCENCE MEASUREMENTS

FIELD OF THE INVENTION

This invention relates generally to fluorescence analytical techniques. More specifically, the invention relates to a method and apparatus for simultaneously measuring the fluorescence of a plurality of samples disposed in a multi well plate; and most specifically, the invention relates to such multiple sample, analytical techniques wherein the contribution of background fluorescence is greatly minimized.

BACKGROUND OF THE INVENTION

Fluorescence measurements are employed in a variety of analyses and in such techniques, illumination of a first wavelength absorbed by a sample induces the sample to emit light of a second wavelength. The wavelength and/or intensity of the secondary emission may be correlated with composition, concentration, physical environment and similar parameters. In one particular class of fluorescence analyses, cells of various tissue types are grown in culture and incubated in a growth medium with a fluorescent dye. The cells will absorb the dye at particular rates, and these rates may be correlated with various physiological functions of the cells such as $K+$ channel activity. A cell which has absorbed dye will typically fluoresce at an enhanced intensity as compared to the growth medium which incorporates that dye. Fluorescent analyses of this type are of significant importance in the pharmaceutical industry since they may be employed to screen a variety of tissue types for interaction with chemical species of pharmaceutical interest.

In an analysis of this type, cells are cultured in a multiple well plate. These plates typically include 48 or 96 wells, each of which comprises a cylinder of approximately 5 millimeters in diameter, closed at one end by an optically transparent bottom surface and open at the other. The cells are cultured in a layer on the bottom surface of the wells with a supernatant layer of growth medium thereabove. Chemical species being assayed are placed into the supernatant liquid together with a fluorescent dye and the effect of the chemical species on cell metabolism is assayed by measuring the fluorescence of the cell layers. Such techniques are well known in the art and are described, for example, in U.S. Pat. Nos. 4,343,782, 4,835,103 and PCT published application WO 90/15317.

In order to measure the fluorescence of the cells, the cell layers are illuminated with light of a first wavelength and emission at a second wavelength is monitored by a photodetector device. Problems arise in this type of an assay because the cell layer is typically on the order of 10 microns in thickness, while the depth of the supernatant liquid is on the order of many millimeters. While the relative intensity of the emission from the supernatant liquid is generally lower than that from the cells which have absorbed the dye, fluorescence from the supernatant liquid constitutes a significant source of error in these assays because of the large volume of the supernatant.

This problem is illustrated by the drawing of FIG. 1 which depicts a particular prior art methodology for fluorescence measurements. Shown in the figure is a well 10 which is typically a part of a larger plate comprising an array of such wells. Disposed within the well 10 is a volume of cell growth medium 12, and a layer of cultured cells 14 is shown atop the bottom surface 16 of the well 10. In the illustrated embodiment, the layer of cells 14 is flooded with illumination 18 which induces fluorescence in the cells 14 as well as in the supernatant liquid 12. A detector 20, typically operating in connection with a lens 22 views the cell layer 14. Generally, the detector 20 and source of the light beam 18 (not shown) are on a common optical axis and share some optical elements such as the lens 22. It will be appreciated from the figure that fluorescence in the supernatant liquid 12 will significantly interfere with the measurement of cell fluorescence.

In order to overcome problems of background fluorescence, the art has employed a microscope to measure the fluorescence of cell layers disposed in a well with a supernatant liquid. The limited depth of focus of the microscope minimizes background fluorescence contributions. FIG. 2 depicts one such prior art approach. As shown therein, a well 10 includes a supernatant growth medium 12 and a cell layer 14 upon the bottom 16 thereof. A microscope, indicated schematically by lens 24 is positioned to view the cell layer 14. It operates in conjunction with a detector 20 to measure the fluorescence of a very small area 26 of the cell layer 14; and as mentioned previously, the source of illumination is generally incorporated into the microscope/detector unit. The extremely limited depth of focus of the microscope 24 permits the detector to "see" only a limited portion of the supernatant liquid and hence only a small portion of the fluorescence therein, indicated by region 28 in the figure, contributes to background noise.

While the approach of FIG. 2 provides acceptable accuracy, the severely restricted field of view of the microscope greatly limits the speed of this technique. A microscope of 40× will give a depth of field of 50 microns, which is adequate to minimize background; but, the field of view of the microscope will be approximately 10 microns. In order to obtain an accurate signal characteristic of K+ channel activity it is necessary to scan a several hundred square micron portion of each well, typically in a raster pattern, to develop a statistically significant signal. Because of the limited field of view of the microscope, the scan takes several minutes. In many studies, it is desirable to update data every few minutes; therefore, the system is limited to measuring a single well over the course of an experiment which may run several hours. Even if only a single scan is made per well, read times for a 96 well plate will be several hours. In addition to the foregoing, microscope arrangements of this type are quite expensive. U.S. Pat. No. 5,097,135 discloses the use of a microscope for making fluorescence measurements of this type. U.S. Pat. No. 5,091,652 discloses a microscope based fluorescence analyzer which operates in a scanning mode.

Thus, it will be seen that there is a need for a fluorescence analyzer which is capable of measuring the fluorescence of a thin cell layer disposed in a well of a multiple well plate, with minimal interference from fluorescence in a supernatant medium. It is further desirable that the analyzer be capable of rapidly measuring the fluorescence of a plurality of samples. It is most desirable that the analyzer be capable of making a large number of measurements in parallel. The present invention, as will be apparent, from the drawings, discussion and description which follow, provides for an improved apparatus and methodology for fluorescence measurements. The present invention minimizes background fluorescence and may be operated to measure, in parallel, the fluorescence of cell layers in each of the wells of a multiple well plate. These and other advantages of the present invention will be readily apparent from the drawings, discussion and description which follow.

BRIEF DESCRIPTION OF THE INVENTION

There is disclosed herein a method for the simultaneous measurement of the fluorescent emission from each of a plurality of samples disposed in a multiple well plate. The method includes the steps of: providing a light source which emits illumination of a first wavelength selected to excite the fluorescent emission of light of a second wavelength by the samples; disposing the light source so as to project illumination of the first wavelength onto a portion of a bottom surface of each of the wells at a first angle of incidence so as to excite the fluorescent emission of light of the second wavelength from the bottom surfaces of the wells. The method includes the further step of disposing an optical sensor, responsive to illumination of the second wavelength so as to receive light emitted from the bottom surface of the wells at a second angle such that at least one of the first or second angles is oblique to the bottom surface of the wells. Because of the angular relationship of the source of illumination and detector, the detector does not view a major portion of the illuminated, fluorescing, supernatant medium.

In particular embodiments, the detector views only a portion of the illuminated cell layer, thereby further restricting background contributions. In some instances, the detector preferably views a rectangular portion of the illuminated cell layer. Illumination of a portion of the bottom surface of each well may be accomplished by disposing a mask between the surface of light and the wells. In other instances, a diffractive element such as a holographic optical element may be employed to restrict and direct the illumination. In one embodiment, the angle of illumination is less than 90° and the viewing angle of the detector is approximately 90° whereas in other instances the illumination is incident upon the well at approximately 90° and the viewing angle of the detector is less than 90°. In some instances the detector is an array of charge coupled devices and the light source may be a laser. The invention also includes apparatus for carrying out the method.

BRIEF DESCRIPTION OF THE DRAWINGS

FIG. 4 is a cross-sectional view of a single well of a multiple well plate as employed in conjunction with another embodiment of the present invention;

FIG. 5 is a cross-sectional view of a single well of a multiple well plate as employed in conjunction with yet another embodiment of the present invention.

DETAILED DESCRIPTION OF THE INVENTION

The present invention includes method and apparatus for the simultaneous or sequential measurement of fluorescent emissions from a plurality of samples disposed in a multiple well plate. The invention provides a particular geometric relationship between the illumination which initiates the fluorescence and the detector which senses the fluorescence. This geometric relationship minimizes background-noise resultant from fluorescence in a supernatant medium and also eliminates cross talk between adjacent wells. The present invention may be implemented in a variety of particular configurations and FIGS. 3A and 3B illustrate one particular embodiment of the present invention.

Figure 1:
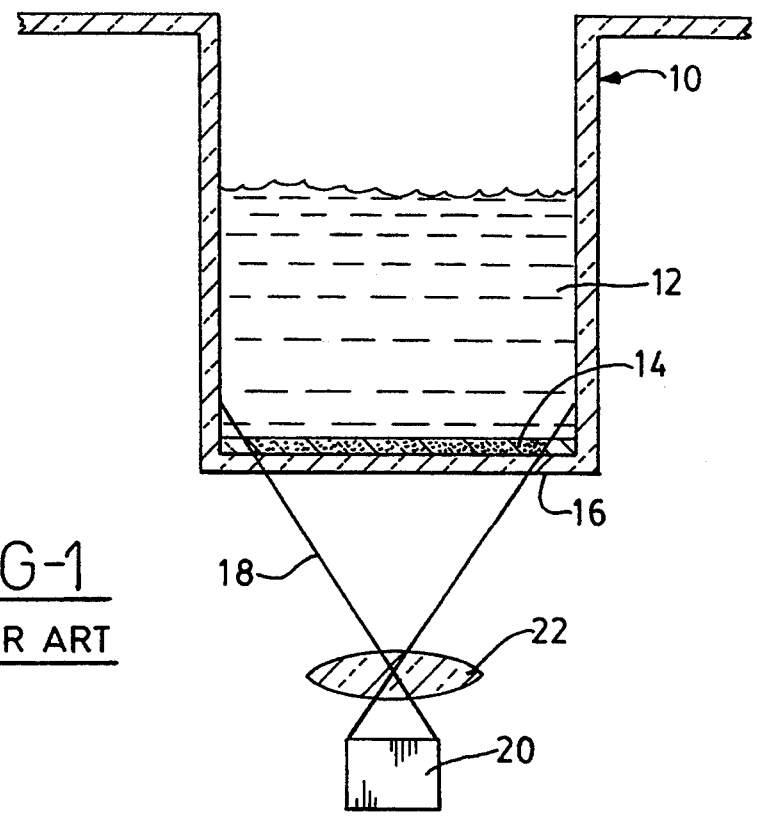
FIG. 1 is a view of a single well of a multiple well plate illustrating a prior art fluorescence measuring technique as used in conjunction therewith.
Figure 2:
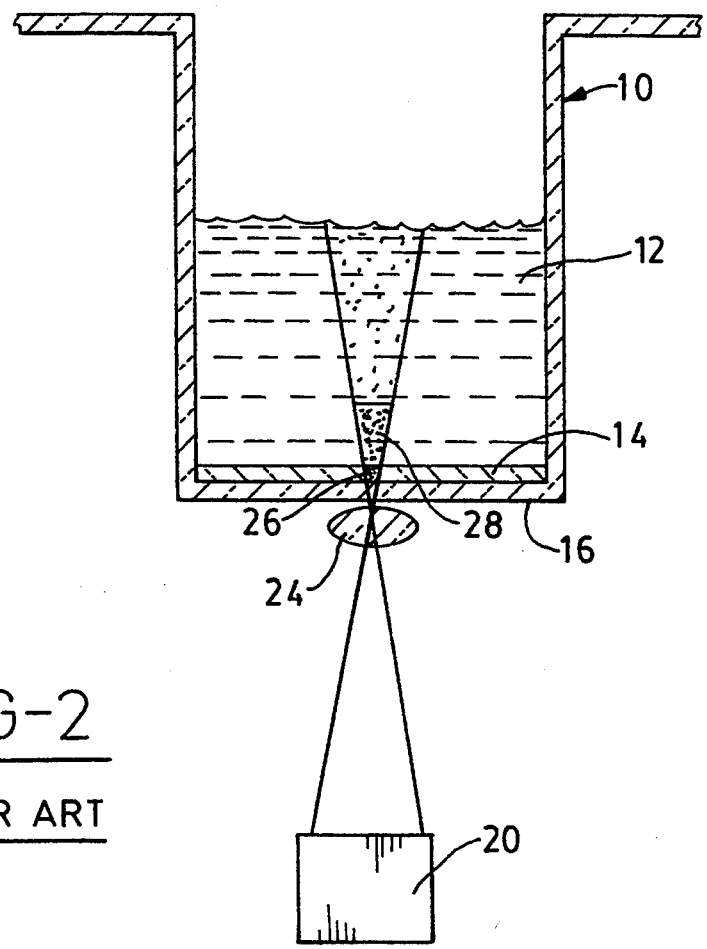
FIG. 2 is a cross-sectional view of a single well of a multiple well plate illustrating a prior art fluorescence measurement technique which includes the use of a microscope.
Figure 3A:
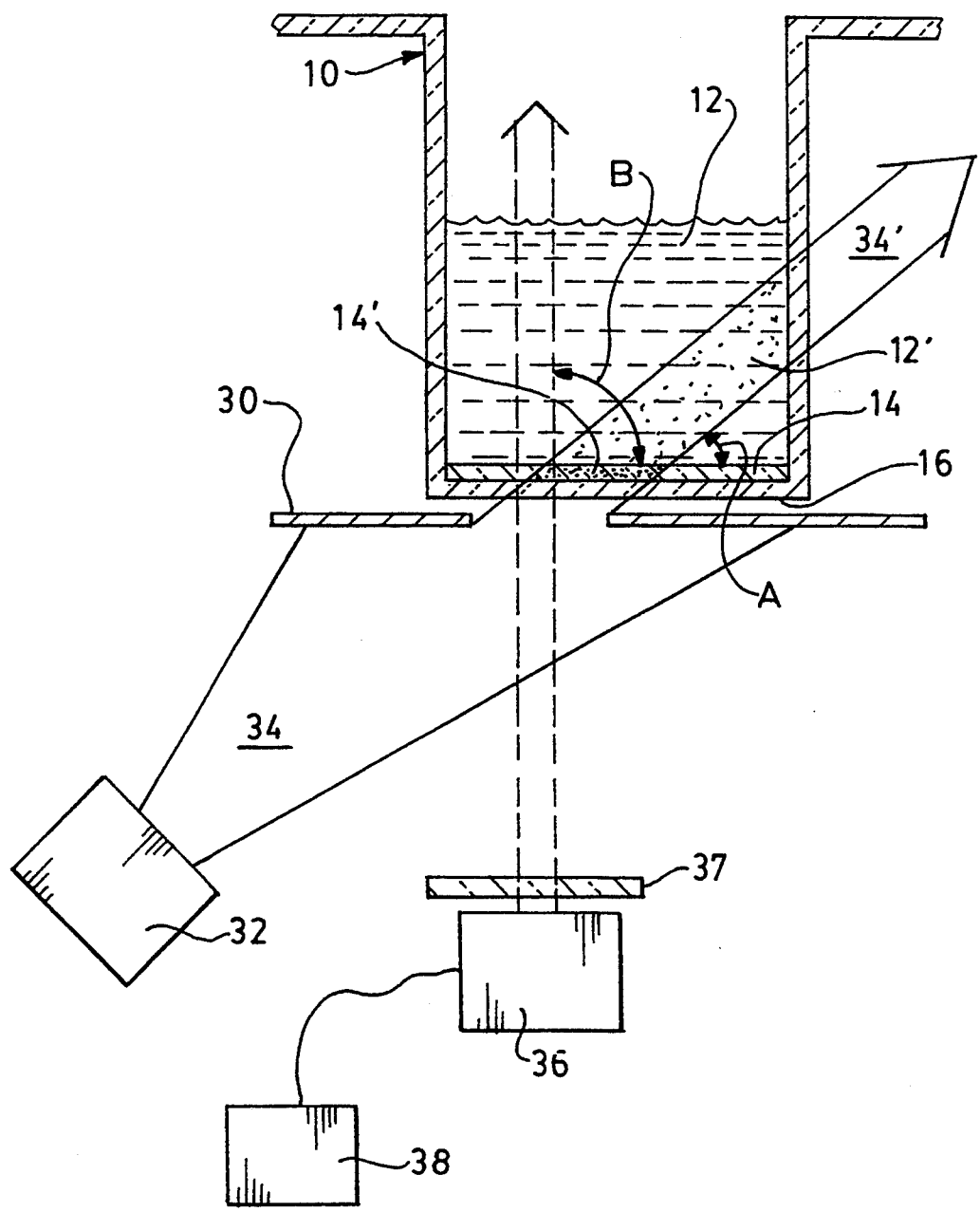
FIG. 3A is a cross-sectional view of a well of a multiple well plate illustrating one embodiment of the present invention as employed for the measuring the fluorescence of a layer of cells disposed on the bottom of the well.
Figure 3B:
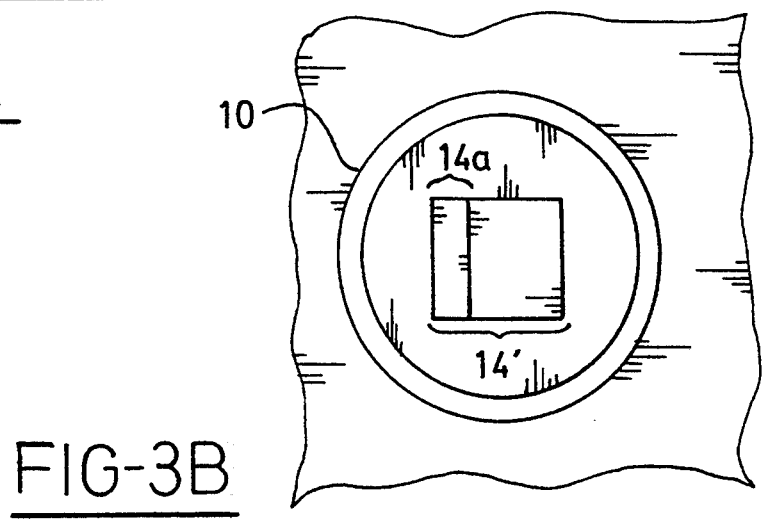
FIG. 3B is a bottom plan view of the well of FIG. 3A illustrating the present invention.

FIG. 3A depicts a well 10 of a multiple well plate, as previously described. Within the well 10 is a layer of cultured cells 14 disposed upon the bottom surface 16 of the well 10. The well 10 is partially filled with a culture medium 12 which also includes a fluorescent dye as well as any chemical composition which is being tested. In accord with the principles of the present invention there is provided a light source 32 disposed so as to illuminate the well with a beam of light 34. A mask 30 is interposed between the light source 32 and well 10 and includes an aperture therein which restricts the amount of light passing into the well.

As illustrated in the figure, the portion 34' of the beam of light 34 which passes through the mask 30 and into the well 10, excites a fluorescent emission in that portion of the cell layer 14' illuminated thereby and in that portion 12' of the supernatant liquid 12 which it strikes. As mentioned hereinabove, when the fluorescence of the illuminated portion of the cell layer 14' is measured, background fluorescence from the illuminated portion of the medium 12' is an unwanted source of interference.

There is also provided an optical detector 36 which is sensitive to the fluorescent emission. The detector 36 is positioned so as to view the illuminated portion 14' of the cell layer, and it will be noted that the beam of illumination 34 strikes the cell layer 14 at an angle of incidence, A, which is less than 90° (i.e., the angle between beam 34' and the cell layer 14), whereas the detector 36 views the illuminated cell layer 14 at an angle, B, which in this instance is approximately 90°. In this manner, the majority of the fluorescence induced that portion of the supernatant liquid 12' struck by the light beam 34' will be out of the field of view of the detector 36. The detector 36 may have a filter 37 associated therewith for absorbing light of the first wavelength, so as to further reduce background signal noise. In one preferred embodiment, the filter 37 is a notch filter which only passes light of the second wavelength.

In accord with the principles of the present invention, illumination of the bottom of the well at a first angle and viewing of the fluorescent emission therefrom at a second angle, where one or the other, or both, angles are oblique to the bottom of the well, minimizes the contribution of background fluorescence. In the illustrated embodiment, the illumination is at an angle of less than 90° and the viewing is at an angle of approximately 90°.

These relationships may be reversed, or otherwise changed in keeping with the principles of the present invention. Furthermore, neither angle need be 90°. The sole requirement is that illumination and viewing angle be selected, and illumination be restricted in areas, so that the detector does not sense large amounts of background fluorescence in the supernatant medium.

It has been found that a further enhancement of the measurement sensitivity may be achieved in the present invention by limiting the field of view of the detector 36 to a somewhat less than the entirety of the illuminated portion 14' of the cell layer 14. Referring now to FIG. 3B there is shown a bottom plan view of the well 10 of FIG. 3A. Visible at the bottom of the well 10 is an illuminated portion 14' of the cell layer. It should be noted that for purposes of the FIG. 3B illustration, the mask 30 has been omitted. In accord with this feature of the present invention, only a relatively small portion 14a of the illuminated portion 14' of the cell layer is viewed by the detector. The illumination in the FIG. 3 embodiment is passing from the left and upward to the right, as illustrated in FIG. 3A; therefore, the left-most portion 14a of the illuminated cell layer 14' will have the least amount of background fluorescence occurring thereabove.

In one preferred version of the FIG. 3 embodiment, the detector 36 comprises an array of charge couple devices disposed within a video camera which is in communication with a signal processor (not shown). The camera is operative to image a plurality of wells simultaneously and the processor analyzes the signal from the detector so as to identify each well and to sense the fluorescent emission therefrom. The processor is programmed to identify those pixels which sense the left edge of the fluorescent emission and to take readings for a predetermined distance therefrom to define the sensed region 14a. In a typical system wherein the wells each have a diameter of approximately 5 millimeters, the illuminated region 14' will be approximately 2 to 3 millimeters on an edge; the sensed region 14a will be coextensive with the width of the illuminated region and will extend 0.1 to 1 millimeters thereinto. The precise dimensions of the illuminated region 14' and the sensed region 14a will vary depending upon the angular geometry employed as well as the relative intensity of the cell fluorescence versus the background fluorescence. In those instances where cell fluorescence is extremely strong and/or background fluorescence is weak, the entirety of the illuminated area 14' may be sensed; whereas in other instances, only a relatively narrow strip will be sensed. In either instance, the sensed area will be far larger than the area typically sensed in a microscope based system.

Other scanning geometries are possible within the scope of the present invention. Referring now to FIG. 4 there is shown a well 10 with a cell layer 14 and a culture medium 12 disposed therein, as previously described. The system includes a mask 30 as previously described; however, the beam of illumination 34 is directed, in this embodiment, to strike the cell layer 14 at an angle C of approximately 90°. Also, the detector 36 is positioned so as to view the illuminated portion 14' of the cell layer 14 at a viewing angle D, of less than 90°. As in the previous embodiment, either all, or a portion of the illuminated cell layer 14' may be viewed by the detector 36. Clearly, other geometric arrangements could be employed in keeping with the spirit of the present invention. For example, it is possible that neither the angle of incidence of the light nor the viewing angle may be 90°. For example, the beam of illumination may come in from the right at an oblique angle to the cell layer and the viewing angle of the detector may be from the left as illustrated in FIG. 4. Control of the angular geometry of the illumination and detection will minimize contributions of background fluorescence in accord with the principles of the present invention.

The FIG. 3 and 4 embodiments illustrate the use of a mask for restricting illumination of the well, through other means may be employed for control of illumination. For example, a diffractive or refractive optical element may be used to control illumination and as illustrated in FIG. 5, a thin optical element such as fresnel lens or a holographic optical element (HOE) 50 is interposed in a light beam 34 to shape and redirect the beam 34' to appropriately illuminate a cell layer 14 in accord with the invention. As illustrated in FIG. 5, a broad beam of illumination 34 strikes the HOE 50 and is narrowed and redirected as a second beam 34' which illuminates the cell layer 14 at the appropriate angle of incidence. A detector 36 is disposed so as to view the illuminated portion 14' of the cell layer 14. Clearly, other variations of this particular geometry may be employed.

Figure 6:
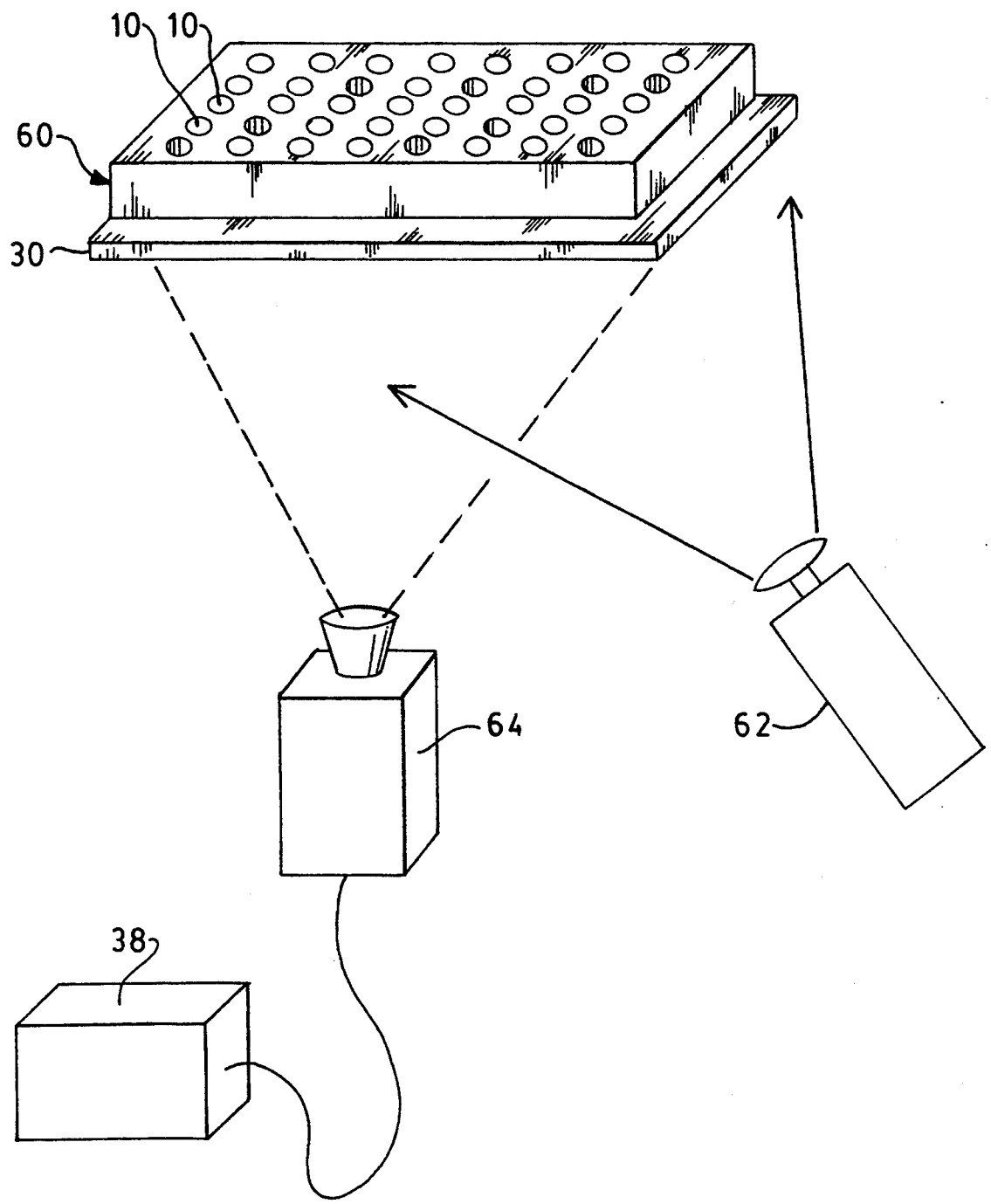
FIG. 6 is a schematic depiction of one embodiment of apparatus for implementing the present invention.

Referring now to FIG. 6, there is shown a stylized depiction of an apparatus structured in accord with the principles of the present invention for purposes of measuring, in parallel, the fluorescence of a plurality of samples disposed in a multiple well plate 60. The plate 60 includes a plurality of wells 10 as generally described herein above. Associated with the plate is a mask 30, as previously described, it being understood that the mask 30 could be replaced by an HOE, Fresnel lens or other such optical element. A light source 62 is disposed to flood the plate 60 with illumination, and this light source 62 is preferably a laser having beam expanding optics associated therewith for purposes of providing flood illumination. The detector in the FIG. 6 embodiment comprises a video camera 64, preferably of the type including a CCD array. The camera 64 has a field of view vide enough to image the entire bottom surface of the well plate 60 at once.

Associated with the camera 64 is a processor 38, as previously described. The processor is operative to digitally analyze the image from the camera. The processor 38 operates on a thresholding basis (based on the noise level of the camera) to detect the edge of each illuminated area having the least amount of background fluorescence and hence the strongest total signal. The processor 38 thereby selects and quantifies the appropriate fluorescence from each well 10 of the plate 60. Use of this technique eliminates the need for precise alignment of the plate with the detection system.

Although not illustrated, it is understood that the system will include appropriate support members for retaining the plate 60, mask 30, light source 62 and detector 64 in the appropriate geometric relationship. In particular embodiments, the system may further include automated plate changing equipment. In many embodiments, the system will include appropriate heating means for maintaining the plate 60 at a preselected temperature so as to stabilize the fluorescent emission and/or provide an optimal regime for cellular respiration.

The present invention provides a significant improvement over previously employed, microscope based systems for quantifying cell fluorescence in multiple well plates. The present invention provides a "telescopic"

approach which is contrast to prior art "microscopic" approaches. The present invention establishes a geometric relationship between illumination and sensing which, together with appropriate masking steps, significantly minimizes contributions from background fluorescence. The present invention allows for the rapid, simultaneous measurement of data from a plurality of wells and greatly enhances the efficiency and costs effectiveness of fluorescent analyses. The foregoing drawings, discussion and description are meant to illustrate the general principles of the present invention and are not intended to be a limitation upon the practice thereof. Numerous modifications and variations of the present invention will be readily apparent to those of skill in the art from the foregoing. Accordingly, it is the following claims, including all equivalents, which define the scope of the invention.

We claim:

1. A method for reducing background fluorescence during the simultaneous measurement of a fluorescent emission from each of a plurality of samples contained in a multiple well plate, each sample being disposed adjacent a background fluorescence producing medium, said method including the steps of:
    providing a light source which emits illumination a first wavelength selected to excite the fluorescent emission of light of a second wavelength by said samples;
    disposing said light source so as to project illumination of said first wavelength onto and through a portion of a bottom surface of each of said wells at a first angle of incidence, so as to penetrate said samples and excite the fluorescent emission of light of said second wavelength therefrom through the bottom surfaces of said wells;
    disposing an optical sensor, responsive to illumination of said second wavelength, so as to receive light emitted from the bottom surface of each of said wells at a second angle wherein at least one of said first or second angles is oblique to said bottom surface so as to increase the extent to which the paths associated with said illumination and said sensing intersect within said sample as compared to said background fluorescence producing medium; and
    sensing the light emitted from the bottom surface of each of said wells with said optical sensor.

2. A method as in claim 1, wherein the step of sensing the light emitted from the bottom surface of each of said wells comprises sensing only a portion of the light emitted from each of said wells.

3. A method as in claim 1, wherein the step of projecting illumination onto a portion of the bottom surface of said wells comprises projecting a rectangular pattern of illumination thereunto.

4. A method as in claim 1, wherein the step of projecting illumination onto only a portion of the bottom surface of each of said wells includes the further step of disposing a mask between the bottom surfaces of said wells and said light source, said mask including a plurality of openings therein.

5. A method as in claim 1, wherein the step of illuminating only a portion of the bottom of each well includes the further step of disposing a diffractive optical element between the bottoms of said wells and the light source, said diffractive element operative to redirect incident light through only a portion of said well at said first angle.

6. A method as in claim 1, wherein said second angle is approximately 90°.

7. A method as in claim 1, wherein said first angle is approximately 90°.

8. A method as in claim 1, wherein the step of disposing an optical sensor comprises disposing an array of charge coupled devices.

9. A method as in claim 8 wherein the step of disposing an optical sensor comprises the step of disposing an optical sensor having a filter associated therewith which is operative to absorb light of said first wavelength.

10. A method as in claim 1, wherein the step of providing a light source comprises providing a light source including a laser.

11. An apparatus for the simultaneous measurement of a fluorescent emission from each of a plurality of samples disposed in a multiple well plate, each sample being supported adjacent a medium capable of contributing to background fluorescence, said apparatus comprising:
    a light source operative to provide illumination of a first wavelength selected to excite the fluorescent emission of light of a second wavelength by said samples, said light source disposed so as to project illumination along a first path onto a portion of a bottom surface of each of said wells at a first angle of incidence, penetrating into each sample so that the samples therein fluorescently emit light of said second wavelength from the bottom surfaces of the wells; and
    an optical sensor, responsive to illumination at said second wavelength, said optical sensor disposed so as to receive light emitted from the bottom surface of each of said wells along a second path at a second angle relative to said bottom surface of each well, said optical sensor being operative to measure the fluorescent emission from each well, said light source and sensor being disposed so that at least one of said first or second angles is oblique to said bottom surface, thereby reducing background fluorescence by increasing the extent to which said first and second paths cross within said samples as compared to said medium.

12. An apparatus as in claim 11, wherein said sensor is operative to sense only a portion of the light emitted from the bottom surface of each well.

13. An apparatus as in claim 11, wherein said light source is operative to illuminate a rectangular portion of the bottom surface of each of said wells.

14. An apparatus as in claim 11, further including a mask having a plurality of openings corresponding to said wells disposed between the bottom surface of said wells and said light source.

15. An apparatus as in claim 11, further including a diffractive optical element interposed between the bottom surface of each of said wells and said light source, said diffractive optical element operative to redirect light incident thereupon through only a portion of the bottom surface of each of said wells.

16. An apparatus as in claim 11, wherein said light source is disposed to illuminate said wells at a first angle of incidence which is approximately 90°.

17. An apparatus as in claim 11, wherein said optical sensor is disposed so as to receive light emitted from the bottom surface of said wells at a second angle which is approximately 90°.

18. An apparatus as in claim 11, wherein said optical sensor is an array of charge coupled devices.

19. An apparatus as in claim 11, wherein said optical sensor has a filter associated therewith which is operative to absorb light of said first wavelength.

20. An apparatus as in claim 11, wherein said light source includes a laser.

21. In an apparatus for the simultaneous measurement of a fluorescent emission from each of a plurality of wells of a multiple well plate, each well including a layer of cells disposed on a transparent bottom surface thereof and a volume of supernatant liquid contained therein, said apparatus including a light source for illuminating each of said wells with light of a first wavelength selected to induce said layer of cells to emit light at a second wavelength and a detector for detecting the light of said second wavelength, wherein the improvement comprises in combination:

said light source being disposed to illuminate the bottom surface of each of said wells with light incident at a first angle and said detector being disposed so as to view the fluorescent emission from each of said cell layers at a second angle, characterized in that at least one of said first or second angles is oblique to said bottom surface so as to increase the extent to which the paths of said projected illumination and Said emitted light cross within said layer as compared to said supernatant liquid.

* * * * *